United States Patent [19]
Rhum et al.

[11] Patent Number: 5,797,906
[45] Date of Patent: Aug. 25, 1998

[54] RETROGRADE TISSUE SPLITTER AND METHOD

[75] Inventors: David Rhum, New York, N.Y.; Rodney Wells, East Lyme, Conn.; Joshua Makower, Nanuet, N.Y.

[73] Assignee: Valleylab Inc, Boulder, Colo.

[21] Appl. No.: 431,368

[22] Filed: Apr. 28, 1995

Related U.S. Application Data

[62] Division of Ser. No. 158,069, Nov. 24, 1993, Pat. No. 5,449,355.

[51] Int. Cl.$^6$ .................................................. A61B 17/39
[52] U.S. Cl. .............................. 606/48; 606/45; 604/107
[58] Field of Search ............................ 606/41, 45, 48, 606/39, 171, 190, 198; 604/104, 106, 107

[56] References Cited

U.S. PATENT DOCUMENTS

| | | |
|---|---|---|
| 2,541,246 | 7/1951 | Held . |
| 3,595,239 | 7/1971 | Petersen . |
| 3,970,088 | 7/1976 | Morrison ................. 606/50 X |
| 4,232,676 | 11/1980 | Herczog . |
| 4,535,773 | 8/1985 | Yoon . |
| 4,601,710 | 7/1986 | Moll . |
| 4,654,030 | 3/1987 | Moll et al. . |
| 4,674,498 | 6/1987 | Stasz . |
| 4,729,374 | 3/1988 | Alfranca ................. 606/171 |
| 4,919,653 | 4/1990 | Martinez et al. . |
| 5,015,227 | 5/1991 | Broadwin et al. . |
| 5,125,928 | 6/1992 | Parins et al. ................. 606/48 |
| 5,133,725 | 7/1992 | Quadri ................. 606/171 X |
| 5,221,281 | 6/1993 | Klicek ................. 606/45 |
| 5,282,813 | 2/1994 | Redha ................. 606/159 |
| 5,300,070 | 4/1994 | Gentelia et al. ................. 606/45 |
| 5,344,420 | 9/1994 | Hilal et al. ................. 606/45 X |
| 5,348,554 | 9/1994 | Imran et al. ................. 606/41 |
| 5,449,355 | 9/1995 | Rhum et al. ................. 606/41 |

FOREIGN PATENT DOCUMENTS

| | | |
|---|---|---|
| 308258 | 9/1988 | European Pat. Off. . |
| WO92 13494 | 8/1992 | WIPO . |

OTHER PUBLICATIONS

Brief Technical Report: "Laparoscopic Needles and Trocars: An Overview of Designs and Complications" by Gary S. Oshinsky, M.D. and Arthur D. Smith, M.D. in Journal of Laparoendoscopic Surgery, vol. 2, No. 2, 1992.

*Primary Examiner*—Jennifer Bahr
*Assistant Examiner*—Eric F. Winaku

[57] ABSTRACT

A device for retrograde hole opening through tissue has a member elongate on an axis with a cross section shaped to insert axially through external tissue. A distal and a proximal end on the member respectively enter the tissue during placement and remain outside the tissue for control. A tip at the distal end has a deployable tissue divider with one or more tissue parting elements and each has a splitter. The tissue parting elements are located within the cross sectional dimensions of the member in a storage position and are movable relative to the tip for placement in an exposed position relative to the tip when shifted from storage so that the splitter thereof splits tissue during retrograde extraction along the axis and contact with tissue. Linkage between the proximal end and the deployable tissue divider retains each of the tissue parting elements with its splitter exposed. The deployable tissue divider has an electrode for transmitting radio frequency energy received from the proximal end to at least each splitter. A return path completes the circuit to provide an electrosurgical effect during the retrograde extraction. A method of placing the device for retrograde hole opening aligns the axis of the elongate member normal to the outside abdominal wall of the body, places the distal end through the tissue and leaving the proximal end outside of the tissue, deploys the tissue divider having one or more tissue parting elements that are first located in a storage position within the cross section to an exposed position with the splitter of each element positioned to split tissue, moves each element axially while exposed and fixed and splits tissue during extraction from the body cavity.

4 Claims, 7 Drawing Sheets

RETROGRADE TISSUE SPLITTER AND METHOD

This is a division, of application Ser. No. 158,069, filed on Nov. 24, 1993, now U.S. Pat. No. 5,449,355.

FIELD OF THE INVENTION

A device for retrograde hole opening through tissue of a human or animal, and more specifically for opening a pathway through external tissue without concern about nicking or cutting internal organs therebeneath.

BACKGROUND OF THE DISCLOSURE

Percutaneous surgery through a trocar inserted cannula and particularly with an opening through the external tissue of an animal or human, such as an abdominal wall has become an important means to minimize the extent of surgical invasion. The lessening of invasion improves the cosmetic result, shortens recovery and lowers the cost. Endoscopic or laparoscopic internal surgical procedures and equipment are available and in use for a variety of medical operations including gall bladder, bowel and gynecological surgery. A proper and simple instrument to safely open the pathway through the external tissue and provide a passage for surgical instruments such as laparoscopes, endoscopes and the like is needed.

U.S. Pat. No. 3,595,239 discloses a catheter tube having an obturator in the form of an electrode passing coaxially therethrough. The obturator electrode is connected to an electrosurgical generator in order to provide high frequency energy used to divide or cut tissue thereby forming a passage for the catheter coaxially about the obturator to pass therewith through the tissue. The tip of the obturator extends beyond the catheter tip and cuts the path for its passage. The catheter moves along with the obturator electrode by means of a ring disposed about the obturator proximal to the tip and inside the tip of the catheter. Disclosure of a safe approach and instrument for opening a pathway is missing.

A copending application incorporated by reference and made a part of this disclosure is U.S. Ser. No. 7-823093, assigned to a common owner. The disclosure in that application has a means for sensing the impedance or load associated with the energy required to do the cutting during insertion of an obturator tip so that the energy may be automatically ceased when the load has changed meaningfully. That approach, although useful with the trocar described therein, may for safe use be augmented by the combination of the circuitry described therein with the needle, stylet or trocar explained in this disclosure.

U.S. Pat. No. 4,232,676 has a knife blade which cuts and cauterizes the incision and in so doing self limits the current and blood flow at the knife. Specifically, the flat scalpel like blade carries electrodes therewith. A flat ceramic insulator supports the electrodes between which radio frequency current flows. Current flows when there is a conductive path between the electrodes. After cutting, the current cauterizes the incision sealing the wound and eliminating the current path. The cutting and coagulation are electrosurgical. The configuration and method for cutting and coagulation electrosurgically is bipolar so no teaching of monopolar cutting and coagulation appears. A monopolar tool and the dangers of changing loads realized upon reaching the inner cavity of the body remain unappreciated in the disclosure of U.S. Pat. No. 4,232,676.

The disclosures of U.S. Pat. Nos. 4,601,710 and 4,654,030, have background which is instructive of the procedures in common use and are therefore incorporated herein by reference and made a part hereof since they explain laparoscopic procedures with obturators in trocar tubes shielded by a sleeve. The obturators include sharpened tips that first pierce the external tissue and carry the trocar coaxially thereabout into the body. The shielding sleeve may project beyond the sharpened tip thereby covering and guarding it after entry into the body cavity. Various automatic mechanical mechanisms are disclosed that activate the shield after penetration. No electrosurgical cutting is taught to lower the effort required of the surgeon to penetrate the body wall. Considerable physical force and subsequent control are needed to effectively place the trocar through the abdominal wall without accidentally puncturing the bowels or other internal organs. The shielding is provided in recognition of the almost impossible dexterity required to make a proper penetration but the shielding has not eliminated the excessive force or the lighting quick reaction needed to drive the sharpened tip inward and stop before contact with an internal organ. Trocars are typically between 5 and 10 millimeters in diameter and the unit loading, (e.g. in units of kilograms per square millimeter) although reduced by the sharpened tip, is significant.

U.S. Pat. No. 4,535,773 discloses techniques for shielding the sharp tip of a trocar by either interposing an extensible shielding sleeve or retracting the trocar into its tube. With regard to the latter, a solenoid operated detent holds the trocar in an extended position relative its tube and electronic sensing in the tip of the trocar is used to activate the detent for release. Nothing in this reference has any disclosure of electrosurgical cutting with a tubular trocar with an impedance responsive circuit to regulate an electrosurgical generator, attached to an electrosurgical cutting tip. The sensors and switches are disclosed in conjunction with a probe which retracts during penetration. In particular, the probe extends beyond the cutting surface until the abdominal wall has been traversed. The sensors can be connected to an audible or visual signal to indicate completion of the puncture. The switches could be mechanical or magnetic, be tripped by a sleeve in the puncturing instrument, a probe or a spring wire protruding from the tip or blade of a sharp pointed cutter. Multiple sensors in the cutting probe and the cannula can be used to signal the penetration position.

U.S. Pat. No. 4,919,653 discloses a device for locating epidural space. The release of force on the tip of a needle triggers an alarm which activate a solenoid latch permitting the needle and its sleeve to move in a cannula in response to an activated electromagnet such that the distal end moves 2 mm into the epidural space. Pressure sensors detect when the depression or release of pressure occurs as the needle enters the epidural space. The pressure signal is converted to produce the voltage difference between the sensor and the potentiometer. This difference is shown on a meter. The pressure sensor can be a small membrane with electrical contacts which are closed in the unloaded position and open when the membrane moves when the epidural space is reached. The passage of current through the contacts keeps the circuit open by means of a relay.

U.S. Pat. No. 2,541,246 discloses a surgical instrument for sphincterotomy with a scissors handle to operate a distal shear. The cutting element is held retracted into the sheath by application of force to the scissors handle so the sheath may inserted through the common bile duct. The scissors handle is moved counterclockwise to open the cutting element and the sheath is withdrawn until the papilla is engaged. The cutting edge is toothed in the nature of a gripper to prevent the tissue from sliding from the grip of the cutting element during shearing. Reversing the movement of the scissors handle, i.e. clockwise, shears the sphincter of Oddi between the cutting element and the sheath. Thus cutting is effected by the scissors actuation of the cutting element not by axial movement of the sheath.

To safely place a cannula by a trocar technique requires knowledge of the position of the distal cutting tip thereof. The cutting edge, at the tip is used to open the passage for the cannula through the animal or human tissue of the abdominal wall. A device to eliminate the need to instantly indicate when the cutting tip has passed through the external tissue and reached the inside of the body is needed so that the internal organs are not injured. Because the organs fill the inside cavity and are close to the wall there is the possibility of injury before the surgeon can stop advancing the distal cutting tip. A lessening of the force required to penetrate will improve control and reduce the likelihood of accidental injury. This is particularly so wherein the control of the energy applied to the electrosurgery is regulated according to load.

It is known to place a Veress needle into the abdominal cavity to inflate the space therein so that the obturator/trocar combination can thereafter be forced through the abdominal wall. The Veress needle is relatively small, i.e. much smaller in diameter than a trocar which is about 10 mm. The distal tip of the Veress needle is typically not needle sharp but may be beveled or chamfered to ease manipulation into position through a scalpel cut through the tough external tissue of the abdominal wall. After placement in the cut and during penetration insufflation gas, typically carbon dioxide, is used to pressurize the abdominal cavity. If a sharp tipped needle is used without the scalpel cut the danger of piercing an internal organ exists so spring loaded shields are needed to protect the patient. With regard to use and design of Veress needles, "The Journal of Laparoendoscopic Surgery, Brief Technical Report", discloses laparoscopic needles and trocars and is referenced herein and incorporated as part of this disclosure.

SUMMARY OF THE DISCLOSURE

To overcome the problems of the prior trocar introduction devices, there is disclosed herein a unique solution which is safe and easy to use. Specifically, a device for retrograde hole opening through tissue may have a member elongate relative to an axis thereof. The member is substantially longer than its cross sectional dimensions. The member is shaped preferably for insertion in a direction generally along its axis through external tissue of a human or animal body during a placement procedure. A distal end and a proximal end are on the member so the distal end first enters the tissue during placement and the proximal end may control the subsequent operation of the device, viz. the deployment and activation of tissue dividing means while remaining outside the tissue. The length of the member may range preferably from 5 to 20 cm. The diameter or cross sectional dimension may range from 1.5 mm to m but smaller sizes are preferred for minimally invasive surgery. Larger diameters are used with procedures and in instruments that require longer incisions.

A tip is associated with the distal end of the member for placement through the external tissue of a human or animal. A deployable tissue divider may have one or more tissue parting elements and each with a splitter; the tissue parting elements may be located within the cross sectional dimensions in a storage position generally carried along and within the cross sectional dimension of the member. Each of the tissue parting elements may be movable relative to the axis for placement in an exposed position when shifted from storage so that the splitter thereof splits tissue during retrograde extraction by contacting tissue during retrograde movement of the member along the axis. Linkage may be positioned between the proximal end and the deployable tissue divider for use in the selective disposition thereof by manipulation of the linkage at the proximal end to position and retain each of the tissue parting elements with its splitter in the exposed position so that upon withdrawal of the member after placement through the external tissue the tissue parting elements enlarges the initial puncture or incision simply while moving retrograde through the tissue, i.e. from the inside to the outside of the body.

In realization of the device that includes piercing in its capabilities, the tip is preferably tapered, beveled or chamfered on an angle to the axis to lessen the insertion force necessary for entry of the member through external tissue. The device is intended to be inserted into the body through an existing passage such as may have been created by piercing or surgical cut down, the tip is preferably either blunt, rounded or of soft material to provide an atraumatic entry through the tissue after cut down with a scalpel incision made to permit access to the softer inside tissue. The member may include a passage therethrough located substantially along the axis of the member for gas or fluid communication between the proximal end and distal end and connecting for fluid communication with a source of fluid flow for moving fluid through the member either toward or away from the distal end and an opening at the distal end for passage of fluid into and out of the patient's body. The member may have a generally circular cross section or may have other cross sectional shapes such as oval, triangular, etc.

The deployable tissue divider might include an electrode insulatively associated with the member for transmitting radio frequency energy received from the proximal end to at least each splitter. An energy supply would be associated with the electrode at the proximal end for supplying radio frequency energy between the proximal end and each splitter. An electrosurgical generator provides radio frequency energy and includes a control to regulate the amplitude and frequency of the energy. A return path connected to the tissue and the energy supply completes the circuit thereby providing an electrosurgical effect during the retrograde extraction through tissue of a human or animal body. The member is preferably a nonconductive electric insulator when the device has electrosurgical capabilities and wherein the return path is between each splitter and the energy supply for completing the circuit and a conductor may be positioned on the member slightly proximal of each splitter for providing bipolar splitting therebetween.

In accomplishing the device that creates the enlarged body access passage by slicing or cutting retrograde rather than by electrosurgery, each splitter is preferably a scalpel for severing tissue during retrograde extraction, that is the splitter has a sharp cutting edge. A handle may be associated with the proximal end for control and manipulation of the distal end and a trigger, button, slider etc. may be carried on the handle for operation of the linkage. A vibrator may alternately be carried within the handle and operatively associated with the linkage to impart motion at each splitter during retrograde extraction for lessening the force needed to extricate along the axis. If required the return path for the electrosurgical device is preferably an electrode pad affixed to the external tissue of the human or animal to form a monopolar electrosurgical circuit across which current flows from each splitter through the tissue.

A resilient load, such as a spring, is in an alternate embodiment of the deployable tissue divider to urge the one or more tissue parting elements from storage to an exposed splitter, and a lock is associated with the linkage to retain the tissue parting elements stored so that upon release of the lock movement of the tissue parting elements relative to the axis of the member is allowed by means of axial motion of the linkage, initiated by force applied to the linkage at the proximal end.

A method of placing a device for retrograde hole opening through the abdominal wall of a human or animal includes preferably aligning an axis of an elongate member generally normal to the outside abdominal surface skin of the human or animal. The step that follows is placing the distal end through the tissue and leaving the proximal end outside of the tissue. A subsequent step is deploying a tissue divider having one or more tissue parting elements first located within the cross sectional dimensions in a storage position to an exposed position wherein a splitter of each the tissue parting elements is positioned to split tissue. It is preferred that a linkage disposed between the proximal end and the deployable tissue divider is used to selectively position and retain the tissue parting elements by manipulation at the proximal end of the tissue parting elements into an exposed position. A further step is moving each of the tissue parting elements with the member while fixed in the exposed position relative to the member after have been shifted from its storage position. An added step may be splitting tissue during extraction from the body cavity so that the splitter parts tissue by contacting tissue while moving retrograde with the member along the axis.

The step of splitting may be performed electrosurgically. The step of deploying the tissue parting elements is possibly performed by swinging the tissue parting elements outwardly from the member. Alternatively, flexible elements may be deployed by moving them out through holes in the member. The step of using the linkage might include the step of pressing a trigger at the proximal end to move the linkage axially through the member and position the tissue parting elements. The step of splitting electrosurgically is alternately performed by applying a return path to the tissue of the human or animal. The step of splitting electrosurgically may be performed by applying a tip that is blunt, rounded or of soft material to atraumatically enter through the tissue after a scalpel incision has been made to permit access to the softer inside tissue or alternatively, may be performed wherein the retrograde hole opening device is combined in a unit with a puncturing tool or a Veress needle.

DETAILED DESCRIPTION OF THE DRAWINGS

Figure 1:
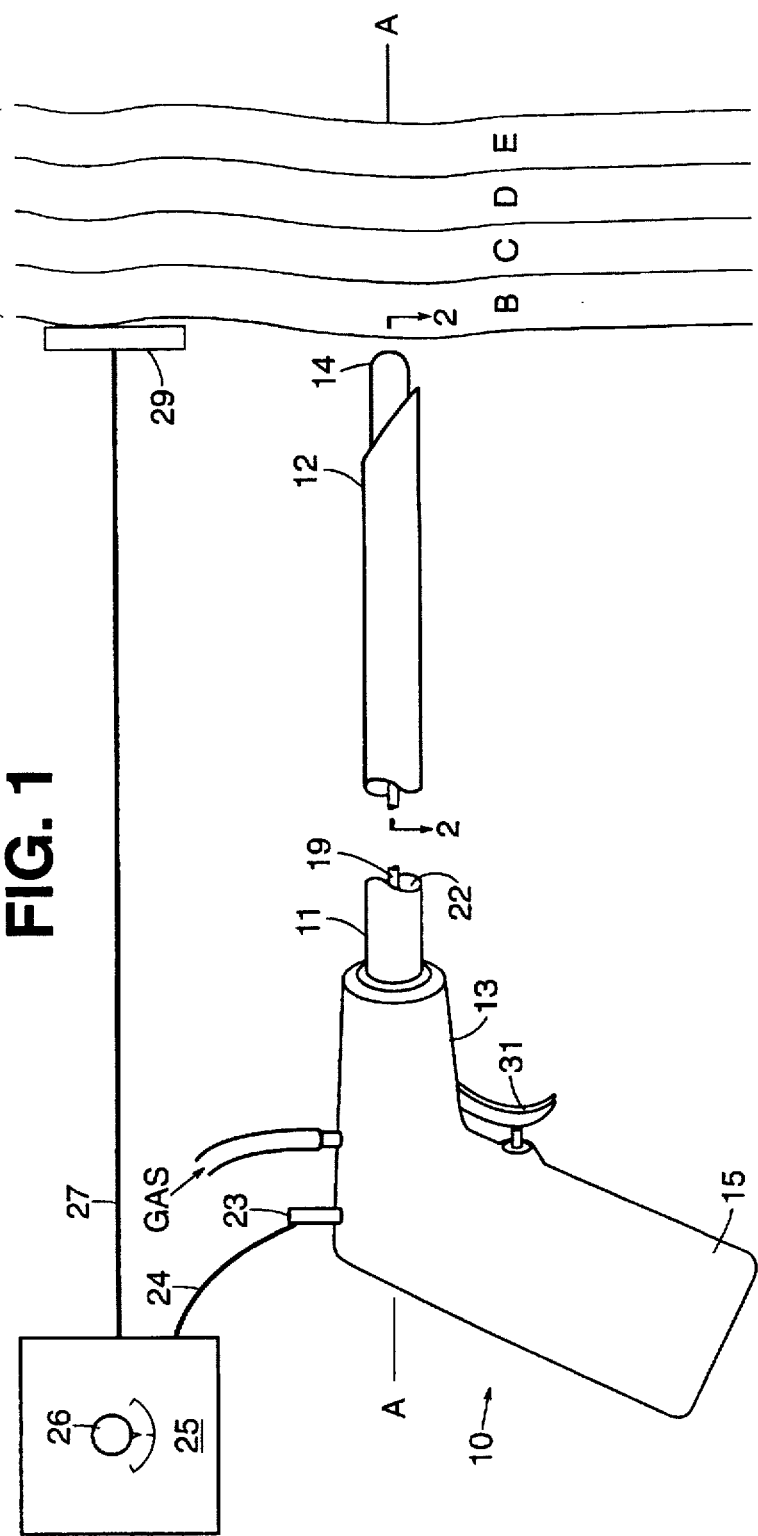
FIG. 1 is a schematic perspective view of the device for retrograde hole opening with a handle at its proximal end and its tip at its distal end; an electrosurgical circuit is also shown.

A device 10 for retrograde hole opening through tissue has in FIG. 1a member 11 elongate relative to an axis "A" thereof. The member 11 is substantially longer than its cross sectional dimensions. The tissue is schematically shown as the skin (B), the muscle (C),fascia/tendon (D), internal surface, e.g. peritoneum (E). The member 11 is shaped for insertion in a direction generally along its axis "A" through external tissue of a human or animal body during a placement procedure which will be described in connection with the steps of the method of use. A distal end 12 and a proximal end 13 are on the member 1 1 and the distal end 12 first enters the tissue during placement. The proximal end 13 remains outside the tissue and has the controls accessible to the surgeon. A tip 14 is associated with the distal end 12 of the member 11 for placement through the external tissue of a human or animal. FIG. 1 is a perspective view of the device 10 for retrograde hole opening with the handle 15 at its proximal end 13 and with its tip 14 at its distal end 12.

Figure 2:
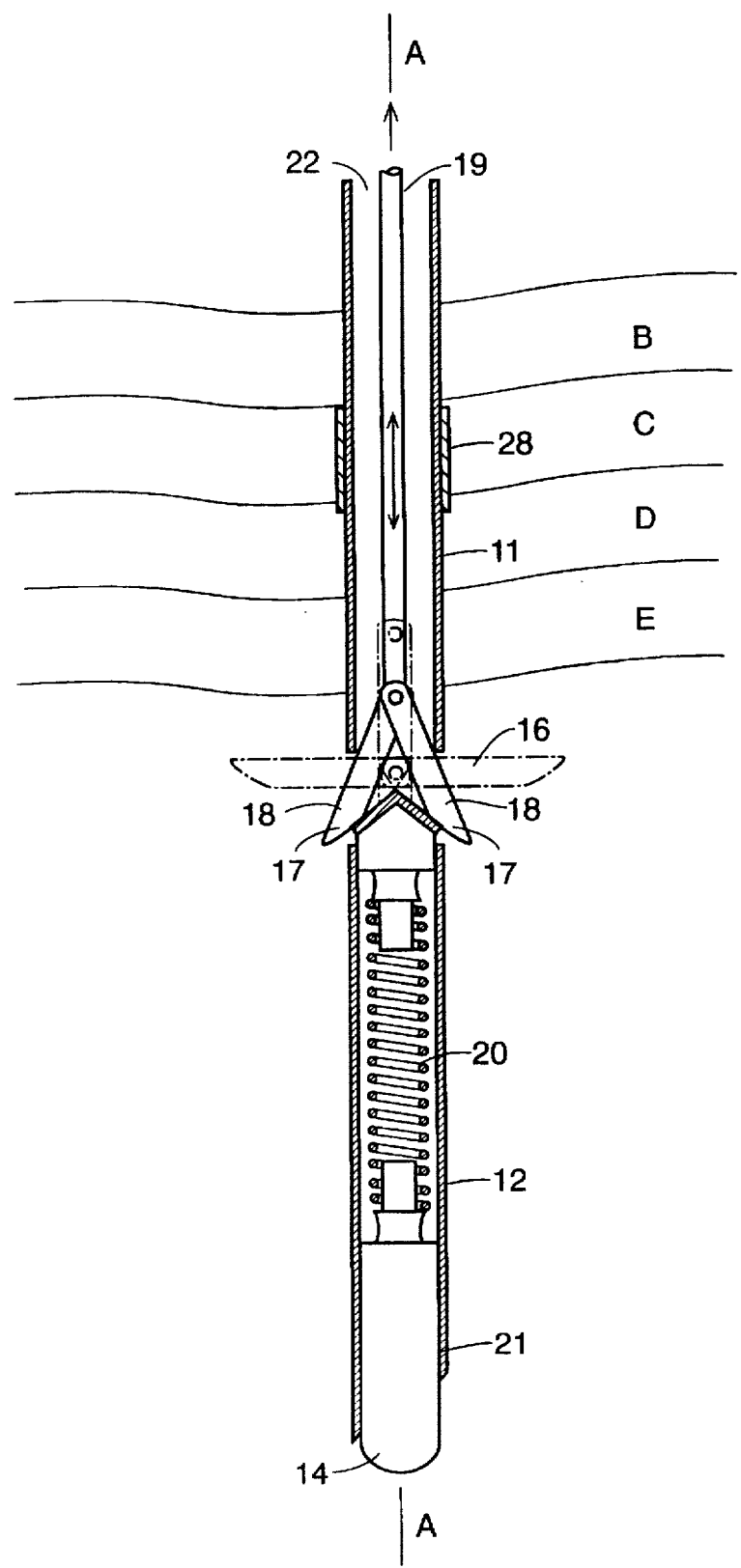
FIG. 2 is an enlarged side view in longitudinal cross section taken along lines 2—2 in FIG. 1 of one embodiment of the tissue part elements of the device of FIG. 1; phantom lines suggest movement from storage.

In FIG. 2a deployable tissue divider 16 can have one or more tissue parting elements 17 and each has a splitter 18. The tissue parting elements 17 are located within the cross sectional dimensions in a storage position generally carried along and within the cross sectional dimension of the member 11. While the divider 16 is primarily for retrograde cutting to enlarge a Veress needle opening, the needle could be about 0.06 to 1.0 cm in diameter or any size that a needle is available in and the tissue parting elements 17 could be extended about 5 mm in opposite directions and more if desired. Each of the tissue parting elements 17 moves relative to the tip 14 during repositioning into the exposed position. The tissue parting elements 17 are shifted from storage so that the splitter or splitters 18, if there are more than one thereof, are located to split tissue during retrograde extraction by contacting tissue during withdrawal of the member 11 along the direction of its axis "A". To understand the shifting of the parting elements 17, the figures show the various alternatives with the tissue parting elements in different states of being shifted from storage to exposed position. FIG. 2 is an enlarged side view in longitudinal cross section taken along lines 2—2 in FIG. 1 of one embodiment having pivoting plates or blades as the tissue parting elements 17. Phantom lines are included in FIG. 2 to show the storage and exposed positions for tissue parting elements 17.

Linkage 19 is positioned between the proximal end 13 and the deployable tissue divider 16 for use in the selective disposition thereof by manipulation of the linkage 19 at the proximal end 13 to position and retain tissue parting elements with their splitters 18 in the exposed position. Upon withdrawal of the member 11, after placement through the external tissue, the tissue parting elements enlarge the initial puncture or incision simply while moving retrograde through the tissue and away from any internal organs. The angle between the splitting edges 18 and the axis A of the member may be in the range between acute, as shown, to a right angle. The splitting edges may be curved, straight or arcuate.

Figure 3:
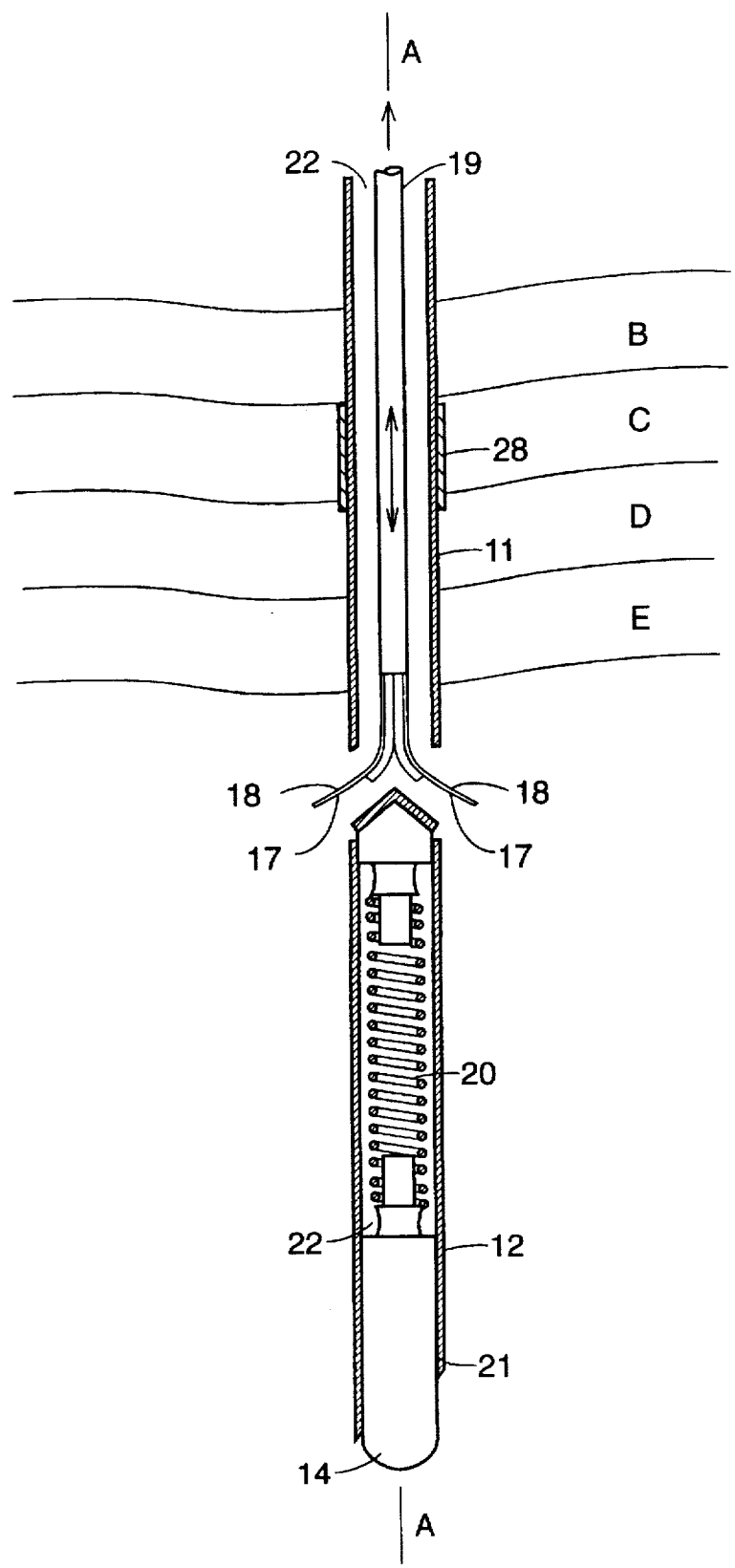
FIG. 3 is an enlarged illustration in longitudinal cross section of the distal end of one embodiment of the device of FIG. 1 wherein the tissue parting elements are shown in cross section with phantom lines to suggest how each is moved from its storage position to its exposed location.
Figure 4:
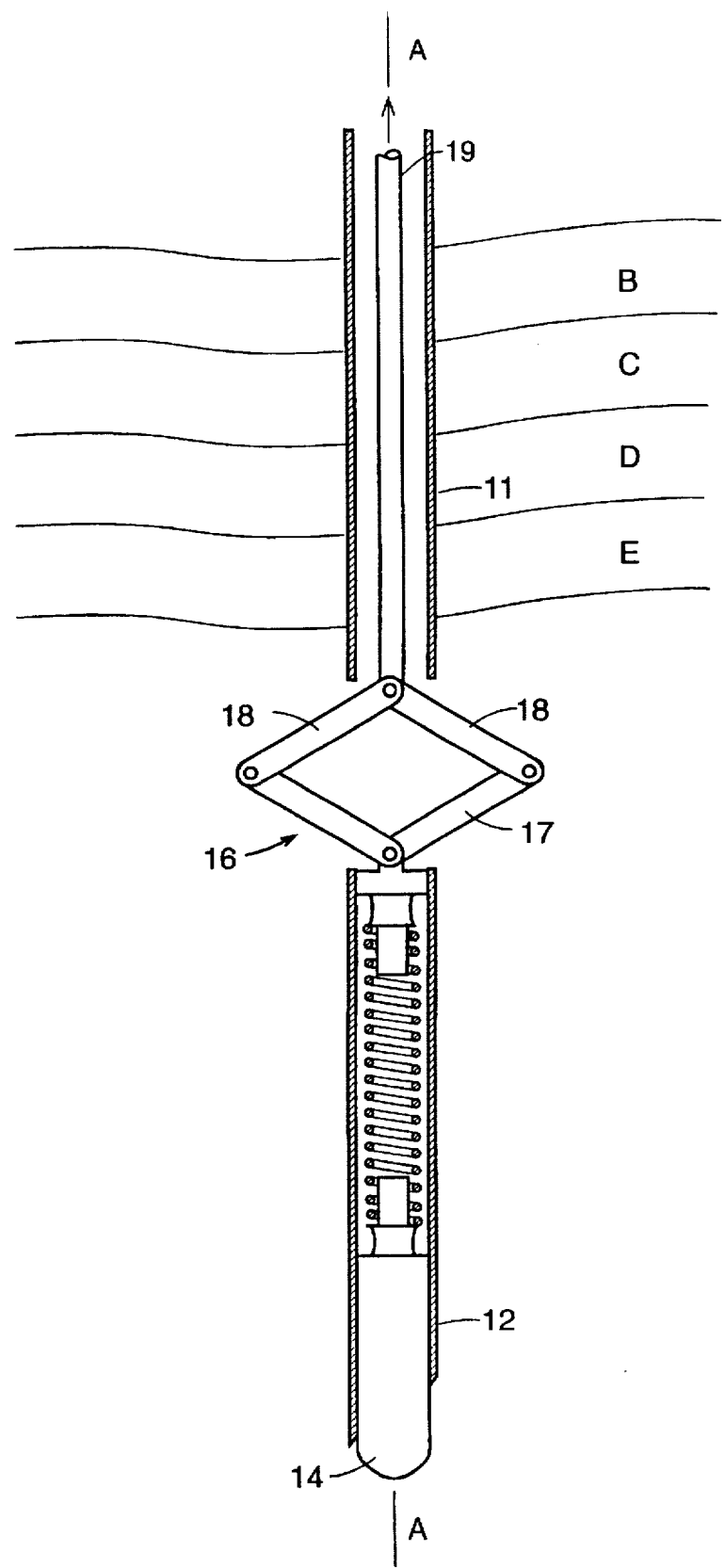
FIG. 4 is an enlarged illustration of the distal end of the device of FIG. 1 wherein another alternate embodiment of the tissue parting elements is depicted.
Figure 8:
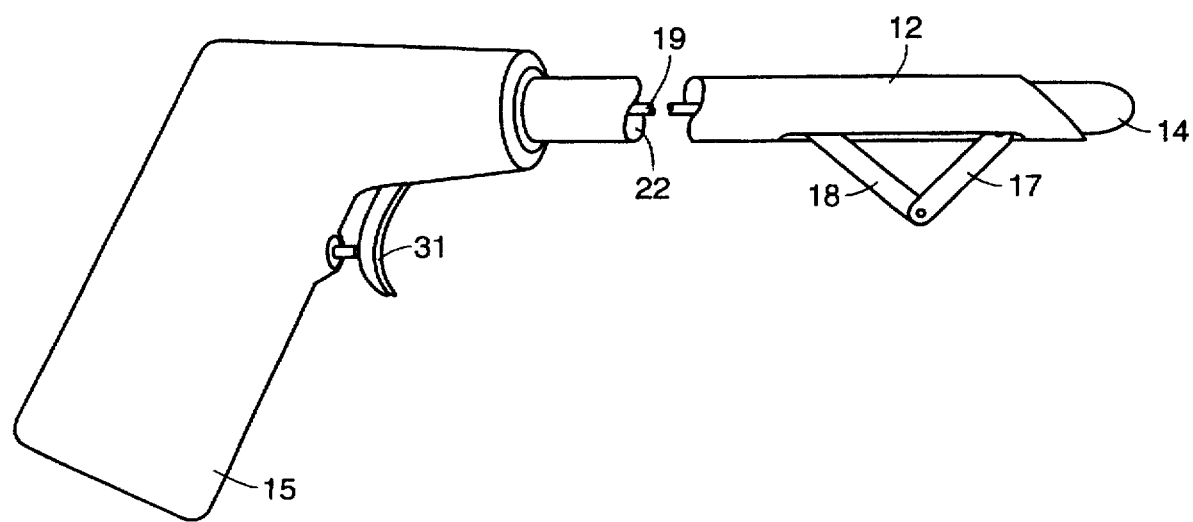
FIG. 8 is an illustration of a retrograde hole opening device with one deployable cutting blade.

FIG. 3 is an enlarged illustration in cross section of the distal end 12 of the device 10 of FIG. 1, as seen along lines 2—2 thereof, wherein the tissue parting elements 17 are wires. The linkage 19 is shown in phantom as lines to depict how they are moved from storage to be exposed. FIG. 4 is an enlarged illustration of the distal end 12 of the device 10 of FIG. 1, as seen along lines 2—2 thereof, wherein another alternate embodiment of the tissue parting elements 17 are depicted to show how a four bar arrangement is spread from its storage position to its exposed location. Specifically, movement of linkage 19 will expand (lateral) and contract (longitudinally) the four bars. FIG. 8 is an illustration of a retrograde hole opening device having a single splitting surface.

The tip 14 is either blunt, rounded or of soft material to provide an atraumatic entry through the external tissue after cut down with an incision made to permit access to the softer inside tissue. Alternately, the tip 14 can be tapered, beveled or chamfered on an angle to the axis "A" to lessen the insertion force necessary for entry of the member 11 through the skin. The Veress related procedure is to use device 10 with a sharp hollow needle, about twelve gauge, with a spring 20 loaded obturator 21, see FIGS. 2 and 3, centrally located in the hollow bore thereof. In placement through the abdominal wall a cut or incision is made through the skin and the needle tip 14 pushed or inserted therethrough. The tissue is relatively easy to pass through and when the passage is complete the spring 20 of the obturator 21 pops it outwardly along axis "A" and thus shields the sharp tip 14 of the Veress needle. Insufflation gas is passed through the needle bore to inflate the abdominal cavity, as in FIG. 1. The tip 14 of the device 10 incorporating the Veress needle is positioned so that the stored tissue parting elements 17 are placed within the abdominal cavity and then shifted into their exposed position for retrograde splitting.

Figure 5B:
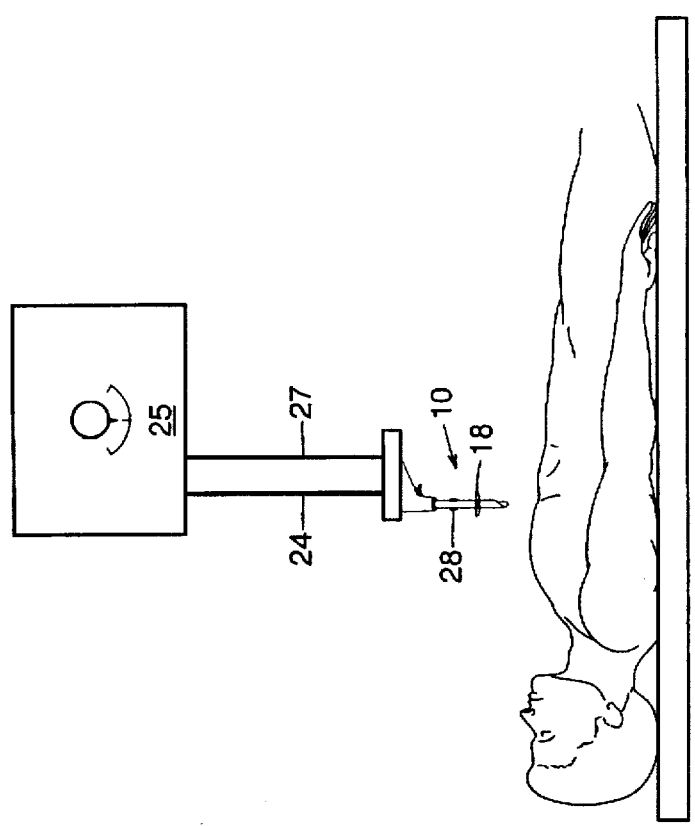
FIGS. 5 are schematic diagrams showing monopolar and bipolar electrosurgical arrangements of the device for retrograde hole opening for use in a circuit with a patient in accord with the method.
Figure 5A:
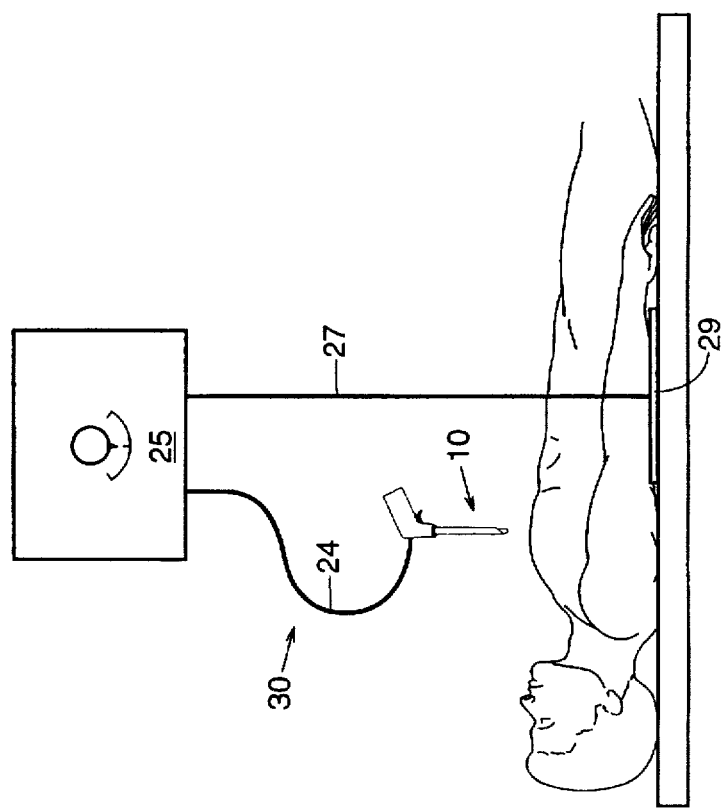

Thus when used as a Veress needle the member 11 includes a passage 22 therethrough located substantially along the axis "A" thereof. The passage 22 is for fluid communication between the proximal end 13 and distal end 12 and for connecting for fluid communication with a source of fluid flow for moving fluid through the member 11 either toward or away from the distal end 12. The fluid for insufflation is carbon dioxide gas. The member 11 has a generally circular cross section but that is not essential. The deployable tissue divider 16 of FIG. 2 or 18 of FIG. 3 include in one embodiment an associated electrode 23 (FIG. 1) insulatively associated with the member 11 for transmitting radio frequency energy received from the proximal end 13 to at least each splitter 18. The cross section of member 11 may be oval semicircular, triangular, etc. An energy supply 24 is associated with the electrode 23 at the proximal end 13 for supplying radio frequency energy between the proximal end 13 and each splitter 18. An electrosurgical generator 25 provides radio frequency energy and includes a control 26 to regulate the amplitude and/or frequency of the energy. In FIG. 1a return path 27 connects to the tissue and the generator 25 to complete a monopolar circuit thereby providing an electrosurgical effect during the retrograde extraction through tissue of a human or animal body. The member 11 is a non conductive electric insulator when the device 10 has electrosurgical capabilities. The return path 27 can be bipolar between each splitter 18. The return path 27 for completing the bipolar circuit is located in the member 11 and in that case a conductor 28 as in FIGS. 2 or 3 can be positioned on the member 11 slightly proximal of each splitter 18 for providing bipolar splitting by electrosurgical energy flow therebetween. To provide greater understanding, FIGS. 5 are schematic views showing monopolar and bipolar electrosurgery for the device 10 and retrograde hole opening as used on a patient in accord with the method. The return path 27 for the monopolar electrosurgical device 10 has an electrode pad 29, see FIGS. 1 and 5, affixed to the external tissue of the human or animal to form a monopolar electrosurgical circuit 30 in FIG. 5 across which current flows from each splitter 18 through the tissue.

Each splitter 18 is alternately, a scalpel for severing tissue during retrograde extraction without electrosurgery. FIGS. 2 or 4 are enlarged side views of the distal end 12 with scalpel blades shown as the tissue parting elements 17 and also illustrated is the tissue surrounding the member with the scalpel blade positioned exposed to split the tissue during retrograde extraction.

Figure 6:
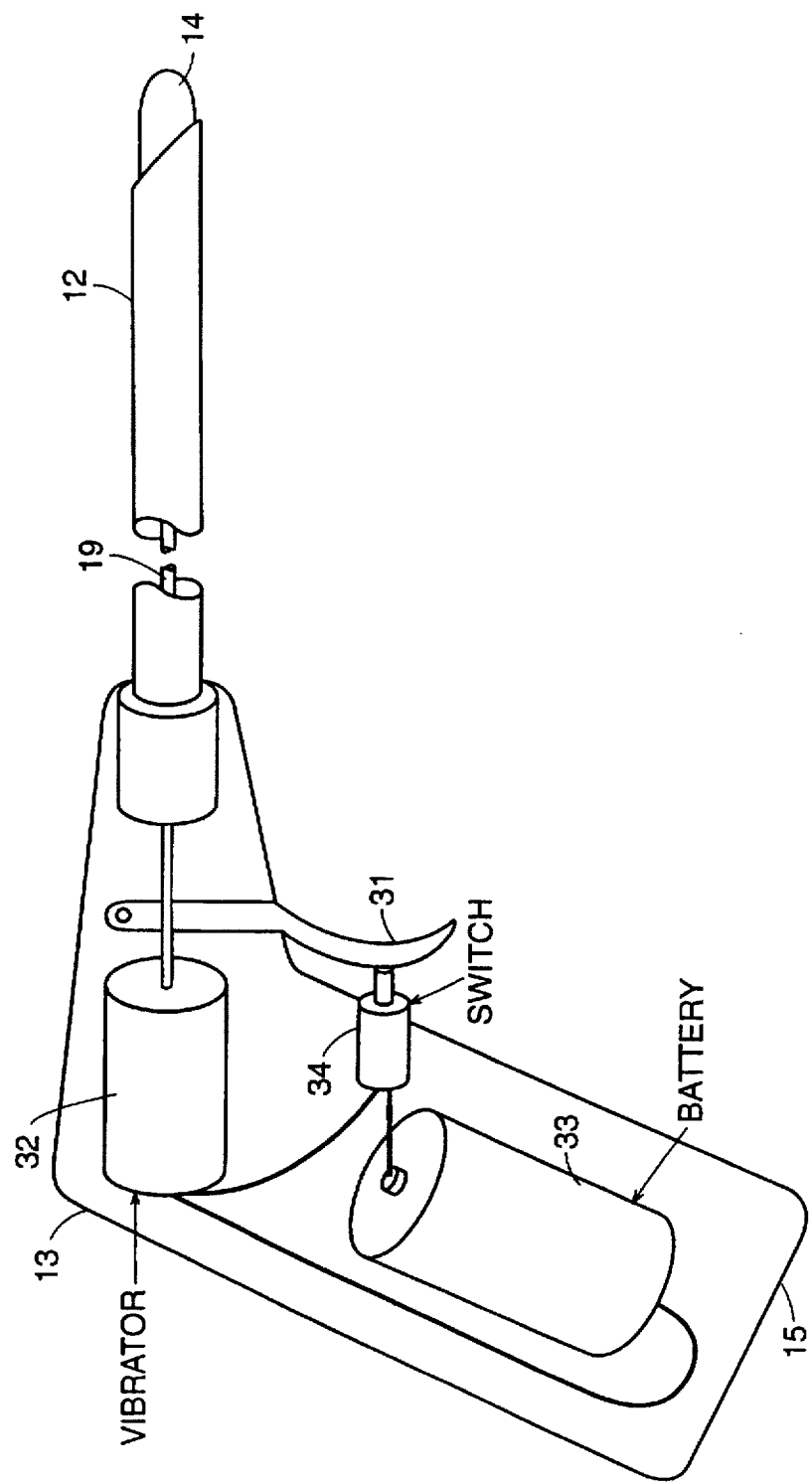
FIG. 6 is an enlarged side view of the handle at the distal end with an electrical vibrator to vibrate the tissue parting elements during retrograde extraction although not shown the vibrator can be a spring motor.

The handle 15, in FIG. 1, is associated with the proximal end 13 for control and manipulation of the distal end 12 and a trigger 31 is carried on the handle 15 for operation of the linkage 19. The handle 15 may be shaped in other ways than as a pistol grip to provide control for the surgeon. The cutters may be activated by button, slider toggle etc. as well as by trigger. In FIG. 6, a vibrator 32 is carried within the handle 15 and operatively associated with the linkage 19 to impart motion at each splitter 18 (not shown in FIG. 6) during retrograde extraction for lessening the force needed to extricate along the axis. The handle 15 is cut away to permit the details of the vibrator 32 and its battery 33 to be seen. The vibrator may be mechanically driven, e.g. spring mechanism, in which case a battery is not needed. A switch 34 is positioned to operate when trigger 31 is disposed.

Figure 7:
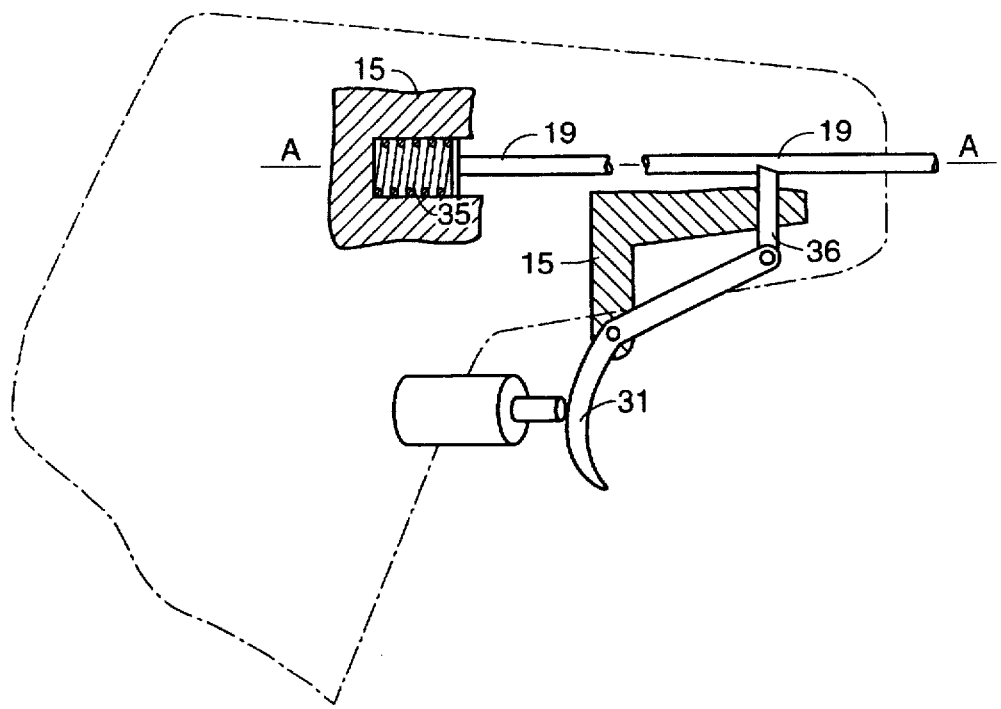
FIG. 7 is an enlarged schematic illustration of inside the handle with the details of the lock to hold the tissue parting elements exposed revealed.

A resilient load 35, e.g. a compression spring, bears in an alternate embodiment, on the deployable tissue divider 16 to urge the one or more tissue parting elements 17 from storage to expose the splitters 18. A lock 36 is associated with the linkage 19 to retain the tissue parting elements 17 stored so that upon release of the lock 36 movement of the tissue parting elements 17 relative to the axis "A" of the member 11 allows the splitters to be set. Force applied to the trigger 31 permits linkage 19 to move axially as illustrated in FIG. 7.

A method of placing the device 10 for retrograde hole opening by a cut down with a scalpel through the abdominal wall of a human or animal includes aligning the axis "A" of the elongate member 11 generally normal to the outside abdominal surface skin of the human or animal. The step that follows is placing the distal end 12 through the tissue and leaving the proximal end 13 outside of the tissue. A subsequent step is deploying the tissue divider 16 having one or more tissue parting elements 17 which are first located within the cross sectional dimensions in their storage position to their exposed position wherein the splitters 18 of each tissue parting element 17 are positioned to part the tissue. Linkage 19 disposed between the proximal end 13 and the deployable tissue divider 16 is used to selectively position and retain the tissue parting elements 17 by manipulation at the proximal end 13. A further step is moving each of the tissue parting elements 17 with the member 11 while fixed in the exposed position relative to the member 11 after each element 17 has been shifted from its storage position. An added step is splitting tissue during the final extraction from the body cavity so that the splitters 18 part tissue by contact therewith while moving retrograde with the member 11 along the axis "A".

Another method step of retrograde splitting is performed electrosurgically. The step of deploying the tissue parting elements 17 is performed by moving the tissue parting elements 17 outwardly from the member 11 swinging FIG. 2 or extrusion FIG. 3. The step of using the linkage 19 includes the step of pressing the trigger 31 at the proximal end to move the linkage 19 axially through the member 11 and position the tissue parting elements 17. The step of monopolar splitting electrosurgically is alternately performed by applying return path 27 to the tissue of the human or animal for the monopolar electrosurgical method. The step of splitting electrosurgically may be performed by initially applying the tip 14 that is blunt, rounded or of soft material to atraumatically entry through the tissue after a scalpel incision has been made to permit access to the softer inside tissue. The device 10 splits electrosurgically and can be inserted with the Veress needle tip and then the abdominal cavity insufflated. Alternatively, a standard Veress needle can be inserted and the abdomen insufflated and then withdrawn leaving a distended abdominal wall. The retrograde hole opening device 10 with non traumatic tip is then inserted without delay through the Veress puncture and the incision made by deploying the cutters/splitters and withdrawing the device 10. Showings of the full penetration through the tissue with the parting elements 17 stored is followed by the tissue parting elements 17 swinging out to expose their splitters 18 and finally the retrograde extraction are suggested by FIGS. 1, 2, 3, 4, and 8.

The device 10 for retrograde hole opening through tissue is not limited to any specific application or a particular tissue parting element. Suitable arrangements or procedures wherein the safety of the patient is assured by retrograde surgery is expected to be protected by the claims. The disclosure is not to limit the use of other materials, structures, techniques, splitting components and procedures or other combinations thereof. So long as retrograde splitting by the safety device such as explained is accomplished, the device or method falls within the scope of the claims of the present disclosure.

What is claimed is:

1. A device for retrograde hole opening through tissue comprising:

a member elongate relative to an axis thereof and being substantially longer than its cross sectional dimensions, the member adapted for insertion through tissue in a direction generally along its axis through external tissue of a human or animal body during a placement procedure and wherein the member includes a passage therethrough located substantially along the axis of the member connected with a source of fluid for moving said fluid through the member;

a distal end and a proximal end on the member, the distal end for first entering the tissue during placement and the proximal end for control of the distal end of the member while remaining outside the tissue;

a tip at the distal end of the member adapted for placement through the external tissue of a human or animal;

a deployable tissue divider having one or more tissue parting elements and each with means for splitting, the tissue parting elements located within a storage position carried within the member, each of the tissue parting elements movable relative to the axis of the member for placement in an exposed position relative to the member when shifted from the storage position so that the means for splitting thereof splits tissue during retrograde extraction by contacting tissue during retrograde movement of the member along the axis and wherein the deployable tissue divider includes an electrode insulatively associated with the member for transmitting radio frequency energy from the proximal end to at least each means for splitting and wherein the member is a non-conductive electric insulator, and a conductor is positioned on the member slightly proximal of each means for splitting for providing an electrosurgical effect therebetween;

an energy supply connecting with the electrode at the proximal end for supplying radio frequency energy between the proximal end and each means for splitting, wherein a return path is between each means for splitting and the energy supply;

an electrosurgical generator for providing said radio frequency energy, the electrosurgical generator including a control to regulate the amplitude and frequency of the energy, and a linkage between the proximal end and the deployable tissue divider for use in the selective disposition thereof by manipulation of the linkage at the proximal end to position and retain each of the tissue parting elements with its means for splitting in the exposed position so that upon withdrawal of the member after placement through the external tissue the tissue parting elements enlarge the initial puncture or incision simply while moving retrograde through the tissue and wherein a handle is associated with the proximal end for control and manipulation of the distal end and a trigger is carried on the handle for operation of the linkage and wherein a resilient load is on the deployable tissue divider to urge the one or more tissue parting elements from storage to the exposed position and a lock is associated with the linkage to retain the tissue parting elements in the storage position so that upon release of the lock, movement of the tissue parting elements relative to the axis of the member is allowed by means of axial motion of the linkage initiated by force applied to the linkage at the proximal end.

2. The retrograde hole opening device of claim 1 wherein the return path is adapted to be connected to the tissue and the energy supply for completing a monopolar circuit thereby providing the electrosurgical effect during the retrograde extraction through tissue of a human or animal body.

3. The retrograde hole opening device of claim 1 wherein the tip at the distal end is soft, blunt or rounded to ease entry through a previously made cut or puncture.

4. The retrograde hole opening device of claim 1 wherein the tip at the distal end is tapered, beveled or chamfered on an angle to the axis to lessen the insertion force necessary for entry of the member through external tissue.

\* \* \* \* \*